(12) United States Patent
Munson (10) Patent No.: US 9,086,358 B2
(45) Date of Patent: Jul. 21, 2015

(54) TEST CELL (71) Applicant: Foresite, Inc., Kokomo, IN (US)

(72) Inventor: Terry L. Munson, Kokomo, IN (US)

(73) Assignee: Foresite, Inc., Kokomo, IN (US)

( * ) Notice: Subject to any disclaimer, the term of this patent is extended or adjusted under 35 U.S.C. 154(b) by 0 days.

(21) Appl. No.: 14/215,494

(22) Filed: Mar. 17, 2014

(65) Prior Publication Data

US 2014/0262771 A1   Sep. 18, 2014

Related U.S. Application Data (60) Provisional application No. 61/787,405, filed on Mar. 15, 2013.

(51) Int. Cl.
*G01N 27/403* (2006.01)
*G01N 27/08* (2006.01)
*G01N 17/00* (2006.01)
G01N 33/00 (2006.01)

(52) U.S. Cl.
CPC .............. *G01N 27/08* (2013.01); *G01N 17/00* (2013.01); *G01N 27/403* (2013.01); *G01N 2033/0095* (2013.01)

(58) Field of Classification Search
CPC .............. G01N 2033/0078; G01N 2033/0095; G01N 27/403; G01N 17/02

USPC ................... 134/2, 11, 21; 15/302; 422/82.01–82.03, 50; 204/400, 409
See application file for complete search history.

(56) References Cited

U.S. PATENT DOCUMENTS

| | | | |
|---|---|---|---|
| 5,783,937 A | 7/1998 | Perraud | |
| 5,783,938 A * | 7/1998 | Munson et al. | 324/71.2 |
| 6,699,384 B1 * | 3/2004 | Lin et al. | 205/792 |

* cited by examiner

*Primary Examiner* — Alexander Noguerola
(74) *Attorney, Agent, or Firm* — Woodard, Emhardt, Moriarty, McNett & Henry LLP (57) ABSTRACT

A test cell for analyzing residue on the surface of a microelectronic component includes a cleaning tip with an opening at one end for passing cleaning fluid into the chamber and for passing used cleaning fluid out of the chamber, and an opening at the other end to access a test area in which cleaning fluid may contact the surface of a component to be tested. A third opening for venting the cleaning tip chamber to the atmosphere may also be provided. A common cleaning/aspiration passageway communicates with the cleaning tip chamber through the first opening. A cleaning passageway provides fresh cleaning fluid to the cleaning/aspiration passageway. An aspiration passageway removes used cleaning fluid from the cleaning/aspiration passageway. An analysis chamber in fluid communication with the aspiration passageway has electrodes effective for qualitatively and/or quantitatively measuring residue removed from the microelectronic surface by the cleaning fluid.

4 Claims, 7 Drawing Sheets

TEST CELL

REFERENCE TO RELATED APPLICATION

This application claims the benefit of U.S. Provisional Patent Application No. 61/787,405, filed Mar. 15, 2013, which is hereby incorporated by reference in its entirety.

BACKGROUND TO THE INVENTION

It is well know to the art that the cleanliness of an electronic assembly is critical to the assembly's field performance and reliability. Unfortunately, corrosive levels of ionic and nonionic residues may build up during the fabrication and assembly processes, and may also arise from external sources during field service. These residues frequently cause electrical shorting or corrosion failures to occur through electromigration or electrical leakage between two circuits.

Since passage of the Clean Air Act in 1987, many new and creative fabrication and assembly processes have emerged and are successfully being used to build hardware. In these modern methods the traditional use of chlorinated solvent cleaners has largely been discontinued, with aqueous, semi-aqueous or new nonchlorinated solvent cleaners now being preferred.

Modern electronic assembly methods are having greater field performance problems, particularly with respect to the contamination referred to above. For example, the new assembly methods which use no rosin or small amounts (<5%) of rosin do not have the protective insulative layer that traditional methods provided. Thus, the new processes are having failures due not to the materials used during assembly, but due to the normal fabrication and handling residues, or because the cleaning was only designed to remove the majority of the flux residue and not the layer of corrosive fabrication residues below the flux or beneath the components. These are new issues for the electronic assembly industry, because it was previously believed that solvent cleaning removed all fabrication and assembly corrosive residues instead of sealing them in with a clear thin layer of rosin.

Although research laboratory analytical tools such as ion chromatography (IC) and high pressure liquid chromatography (HPLC) may be used to separate, identify and quantify the ionic and nonionic residues present on electronic circuit assemblies, these are not production floor process control tools. The current inventive process control tools were developed for monitoring rosin flux and solvent cleaning residues, and are not capable of measuring the true cleanliness of an electronic assembly. Instead, current process control tools are merely gross performance indicators (trend tools) of the processing equipment. With these trend tools, less than 30% of the residues come into solution during extraction, and generally a layer of flux residue, as well as fabrication residue, remains below this layer.

More particularly describing the prior art methods, most prior art trend tools use a solvent water (75% isopropyl alcohol and 25% water) extraction for 5-15 minutes at room temperature or at a slightly elevated temperature (limitation due to flammability), followed by measuring the total change in the conductivity of the solution over the time of the test. The resulting conductivity change is then compared to a conductivity salt standard (e.g., sodium chloride at about 750 ppm). There is no differentiation between corrosive and noncorrosive residues.

One further disadvantage of most prior art methods is that they are designed to extract whole- or half-board areas, and then to normalize the data to provide per unit area calculations (so much NaCl equivalents per square inch). Thus, those prior art methods are not effective for performing comparative cleanliness analysis (for corrosive residues) of various processing step effects, such as: (1) wave solder area vs. surface mount area; (2) top of board after wave solder vs. bottom of board; (3) bare incoming vs. assembled areas; (4) reworked areas vs. non-reworked areas, etc.

It can be seen from the above that a need exists for an improved, nondestructive spot extractor for IC and HPLC analysis to determine the actual contamination levels in specific areas on the board. The present invention addresses that need.

SUMMARY OF THE INVENTION

According to one embodiment of the present invention there is provided a test cell (10) for analyzing residue on the surface of a microelectronic component, comprising:
 a) a cleaning tip chamber (11) having:
  i) a first opening (12) for passing fresh cleaning fluid (steam) into the chamber and for passing used cleaning fluid (steam) out of the chamber,
  ii) a second opening (13) bounded by an end seal (15) and defining a test area in which cleaning fluid (steam) may contact the surface of a component to be tested, and
  iii) a third opening (14) for venting the cleaning tip chamber to the atmosphere;
 b) a common cleaning/aspiration passageway (16) communicating with said cleaning tip chamber through said first opening and effective for providing fresh cleaning fluid (steam) to said cleaning tip chamber and for removing used cleaning fluid from said cleaning tip chamber,
 c) a cleaning passageway (17) for providing fresh cleaning fluid (steam) to said cleaning/aspiration passageway;
 d) an aspiration passageway (18) for removing used cleaning fluid from said cleaning/aspiration passageway; and
 e) an analysis chamber (20) in fluid communication with said aspiration passageway, said analysis chamber having one or more test electrodes (21) disposed therein, wherein said test electrodes are effective for qualitatively and/or quantitatively measuring residue removed from the microelectronic surface by the cleaning fluid (steam).

DESCRIPTION OF PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As previously indicated, one embodiment of the present invention provides a test cell for analyzing residue on the surface of a microelectronic component. The test cell preferably comprises a cleaning tip chamber having a first opening for passing fresh cleaning fluid (preferably, steam) into the chamber and for passing used cleaning fluid (steam) out of the chamber. The test cell also preferably comprises a second opening bounded by an end seal and defining a test area in which cleaning fluid (steam) may contact the surface of a component to be tested. The test cell also preferably comprises a third opening for venting the cleaning tip chamber to the atmosphere.

A common cleaning/aspiration passageway communicating with said cleaning tip chamber through said first opening and effective for providing fresh cleaning fluid (steam) to said cleaning tip chamber and for removing used cleaning fluid from said cleaning tip chamber, is also included.

The preferred device further includes a cleaning passageway for providing fresh cleaning fluid (steam) to said cleaning/aspiration passageway.

The preferred device further includes an aspiration passageway for removing used cleaning fluid from said cleaning/aspiration passageway may be included.

There is also preferably an analysis chamber in fluid communication with said aspiration passageway. The analysis chamber may have one or more test electrodes disposed therein, wherein said test electrodes are effective for qualitatively and/or quantitatively measuring residue removed from the microelectronic surface by the cleaning fluid (steam).

The inventive test cell may further include a venting passageway communicating with said cleaning tip chamber through said third opening and effective for venting the cleaning tip chamber to the atmosphere.

The end seal may define a test area of between about 10 mm$^2$ and about 50 mm$^2$. More preferably, the end seal may define a test area of about 18 mm$^2$.

In one embodiment the test cell includes one or more vent "blocks" in the vent passageway. The purpose of these blocks is to disrupt the flow of any liquid through the vent passageway. In one preferred embodiment the blocks are provided in offsetting pairs, and each block in the pair is approximately 1/16" long and rises to or just above the centerline of the vent passageway. This leaves a space between each block and the opposite side of the vent passageway of approximately 1/16." The blocks of each pair preferably alternate with respect to the side of the passageway in which they are located, so that travel through the blocks requires a serpentine flow.

The vent blocks are provided to reduce the amount of liquid lost through the vent opening. As the vapor/liquid mixture of steam and droplets passes through the vest passageway, liquid droplets encounter the vent blocks and at least some of the liquid ceases to flow through the passageway—instead dropping back into the solvent removal passageway.

If one set of blocks is used, the bocks are preferably positioned near the lower end of the vent passageway. If additional sets are used, the second and third sets are preferably provided in the angled portion of the vent. One or more additional pairs of vent blocks may be provided in other sections of the passageway, such as at or near the vent outlet.

In one embodiment of the present invention the test cell comprises an electrode having an electrode surface, and covered at one end by capillary cover that is spaced apart from the electrode surface a small distance effective to cause cleaning fluid to be drawn into and up in the capillary passageway by capillary forces when the test cell is positioned on an assembly that has cleaning fluid on its surface. The capillary passageway is formed by providing a capillary cover over a portion of the electrode surface 21, with the capillary cover being spaced apart from the electrode a distance effective to cause cleaning fluid to be drawn into and up in the capillary passageway by capillary forces. A gap is accordingly provided between capillary cover member and the electrode surface.

Figure 1:
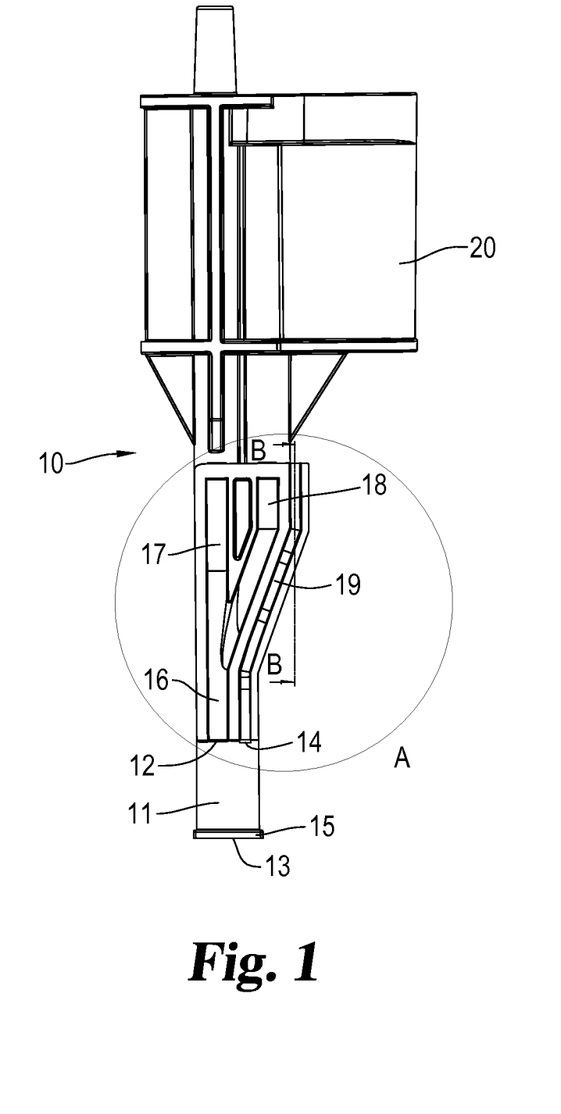
FIG. 1 shows one embodiment of the test cell of the present invention.

Referring now to the Figure, FIG. 1 shows one preferred embodiment of the inventive test cell. Test cell 10 is effective for analyzing residue on the surface of a microelectronic component. The illustrated test cell comprises:

a) a cleaning tip chamber 11 having:
   i) a first opening 12 for passing fresh cleaning fluid (steam) into the chamber and for passing used cleaning fluid (steam) out of the chamber,
   ii) a second opening 13 bounded by an end seal 15 and defining a test area in which cleaning fluid (steam) may contact the surface of a component to be tested, and
   iii) a third opening 14 for venting the cleaning tip chamber to the atmosphere;

b) a common cleaning/aspiration passageway 16 communicating with said cleaning tip chamber through said first opening and effective for providing fresh cleaning fluid (steam) to said cleaning tip chamber and for removing used cleaning fluid from said cleaning tip chamber, c) a cleaning passageway 17 for providing fresh cleaning fluid (steam) to said cleaning/aspiration passageway;

d) an aspiration passageway 18 for removing used cleaning fluid from said cleaning/aspiration passageway; and e) an analysis chamber 20 in fluid communication with said aspiration passageway, said analysis chamber having one or more test electrodes 21 disposed therein, wherein said test electrodes are effective for qualitatively and/or quantitatively measuring residue removed from the microelectronic surface by the cleaning fluid (steam).

The illustrated test cell further includes a venting passageway 19 communicating with said cleaning tip chamber through said third opening and effective for venting the cleaning tip chamber to the atmosphere. Vent blocks 24 are illustrated in vent passageway 19.

The end seal of the illustrated test cell defines a test area of between about 10 mm$^2$ and about 50 mm$^2$. In particular, the end seal of the illustrated test cell defines a test area of about 18 mm$^2$.

Figure 2:
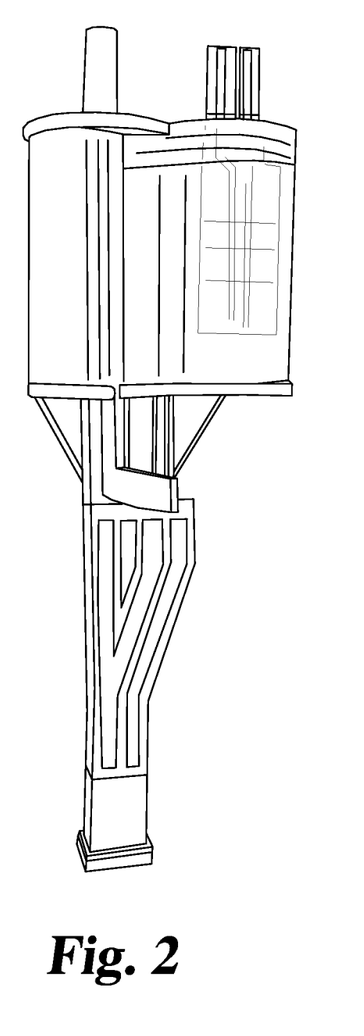
FIG. 2 shows another embodiment of the test cell of the present invention, with the electrode provided in the analysis chamber.

FIG. 2 shows another embodiment of the test cell of the present invention, with electrode 21 provided in analysis chamber 20.

Figure 3:
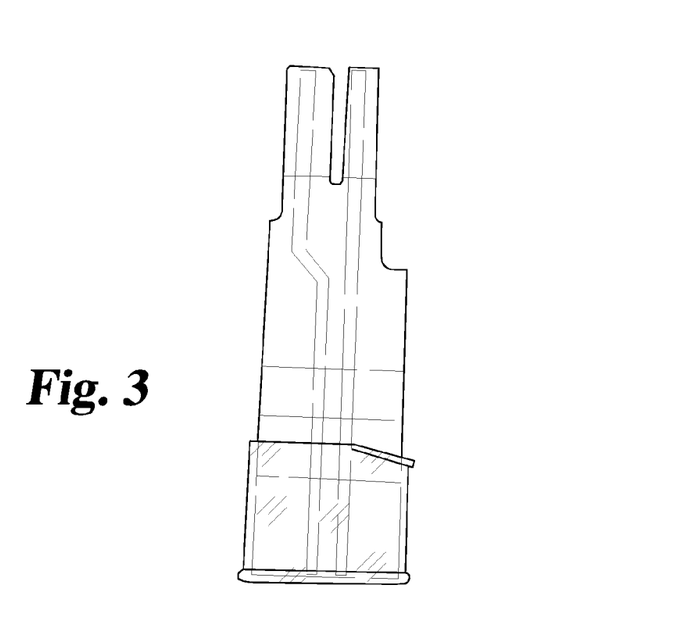
FIG. 3 shows an electrode used in one embodiment of the test cell of the present invention.

FIG. 3 shows an electrode that is preferably positioned in the analysis chamber 20 of the inventive test cell. Electrode 21 is effective for qualitatively and/or quantitatively measuring residue removed from the microelectronic surface by the cleaning fluid (steam).

Figure 4:
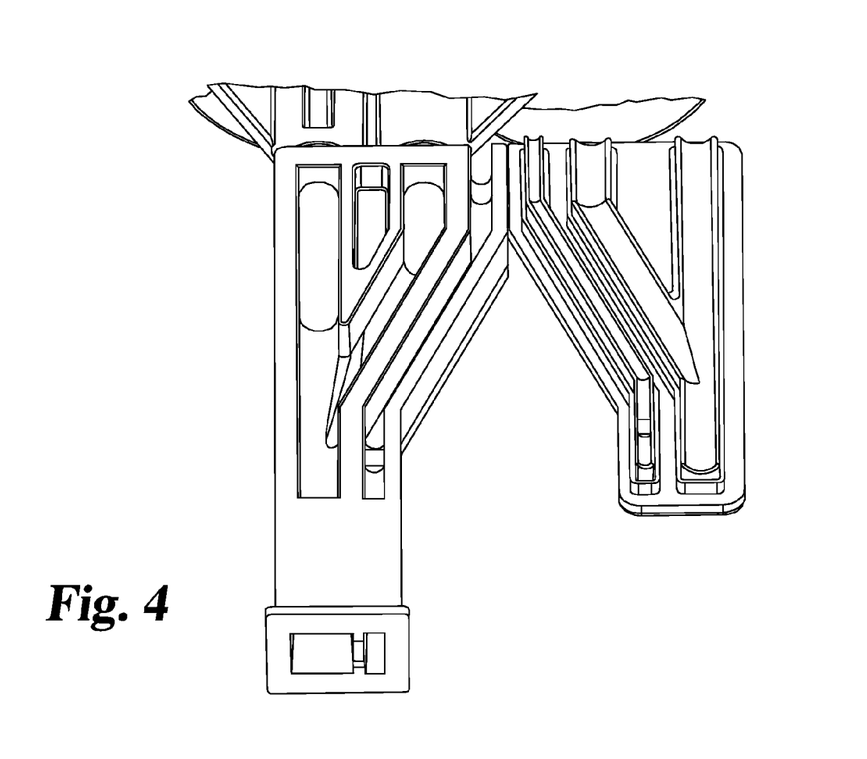
FIG. 4 shows a first view of the interior of a portion of the passageways used in one embodiment of the present invention, including one embodiment of the vent blocks optionally used in the vent passageway of the test cell.

FIG. 4 shows a first view of the interior of a portion of the passageways used in one embodiment of the present invention, including one embodiment of the vent blocks optionally used in the vent passageway of the test cell. Vent blocks 25 are provided on each side of the passageway, and extend only about half-way across the passageway so that fluid may flow through the passageway.

Vent blocks 25 are positioned in the passageway in a manner effective to disrupt the flow of any liquid through the vent passageway. In the illustrated embodiment the blocks are provided in offsetting pairs, and each block in the pair is approximately 1/16" long and rises to or just above the centerline of the vent passageway. This leaves a space between each block and the opposite side of the vent passageway of approximately 1/16." The blocks of each pair preferably alternate with respect to the side of the passageway in which they are located, so that travel through the blocks requires a serpentine flow.

Figure 5:
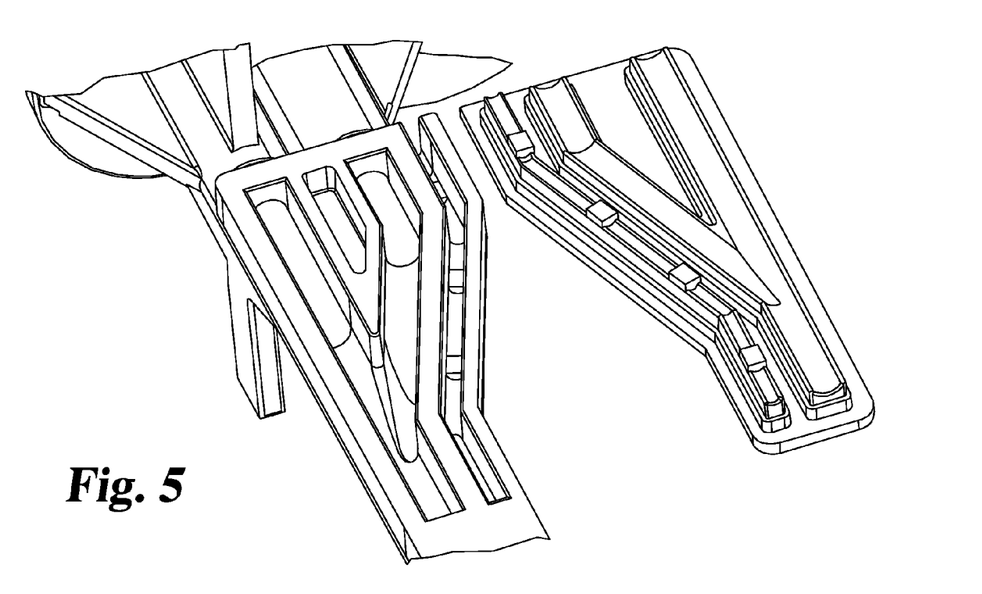
FIG. 5 shows a further view of the interior of a portion of the passageways used in one embodiment of the present invention, including one embodiment of the vent blocks optionally used in the vent passageway of the test cell.

FIG. 5 shows a further view of the interior of a portion of the passageways used in one embodiment of the present invention, including one embodiment of the vent blocks optionally used in the vent passageway of the test cell.

Figure 6:
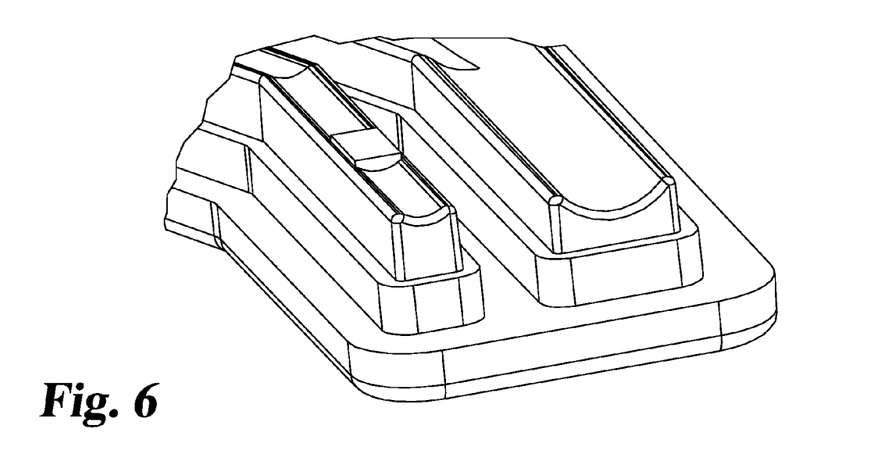
FIG. 6 shows a further view of the interior of a portion of the passageways used in one embodiment of the present invention, including one embodiment of the vent blocks optionally used in the vent passageway of the test cell.

FIG. 6 shows a further view of the interior of a portion of the passageways used in one embodiment of the present invention, including one embodiment of the vent blocks optionally used in the vent passageway of the test cell.

Figure 7:
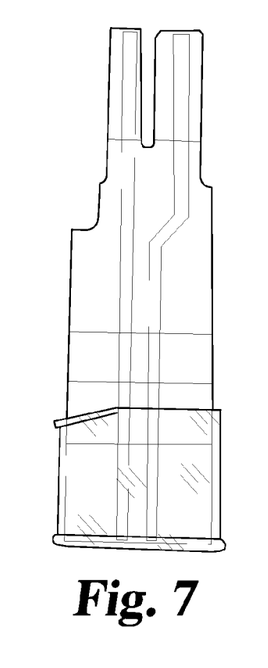
FIG. 7 shows a first view of an electrode with a capillary passageway as used in a second embodiment of the test cell of the present invention.

FIG. 7 shows a first view of an electrode with a capillary passageway as used in a second embodiment of the test cell of the present invention. In the illustrated embodiment electrode 21 has a lower portion that includes a capillary passageway 27. Capillary passageway 29 is spaced a small distance from the surface of electrode 21 so that liquid will be drawn into and up in the capillary passageway by capillary forces.

Figure 8:
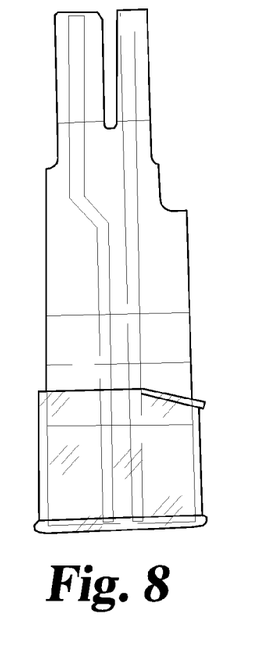
FIG. 8 shows another view of an electrode with a capillary passageway as used in a second embodiment of the test cell of the present invention.

FIG. 8 shows another view of an electrode with a capillary passageway as used in a second embodiment of the test cell of the present invention.

Figure 9:
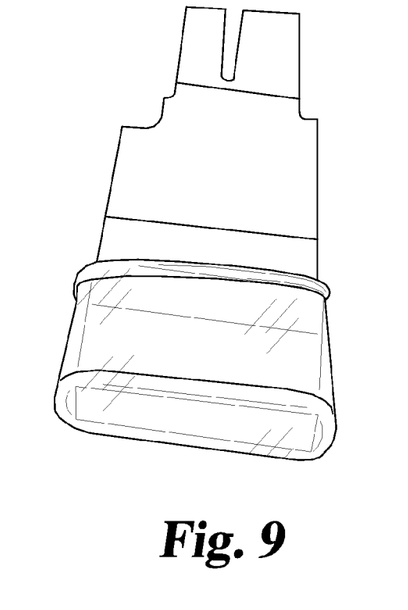
FIG. 9 shows another view of an electrode with a capillary passageway as used in a second embodiment of the test cell of the present invention.
Figure 10:
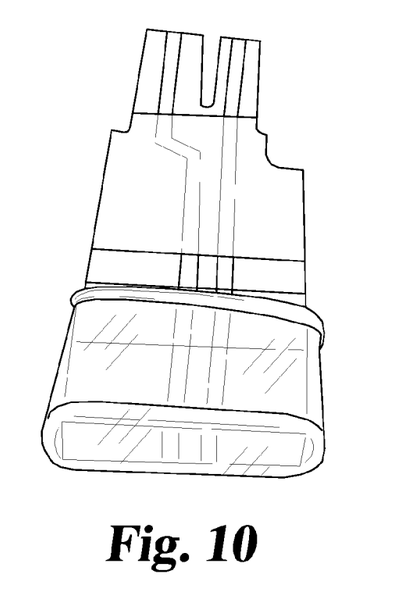
FIG. 10 shows another view of an electrode with a capillary passageway as used in a second embodiment of the test cell of the present invention.
Figure 11:
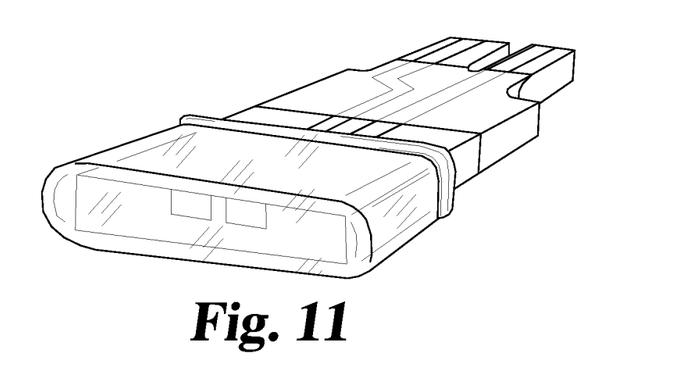
FIG. 11 shows another view of an electrode with a capillary passageway as used in a second embodiment of the test cell of the present invention.
Figure 12:
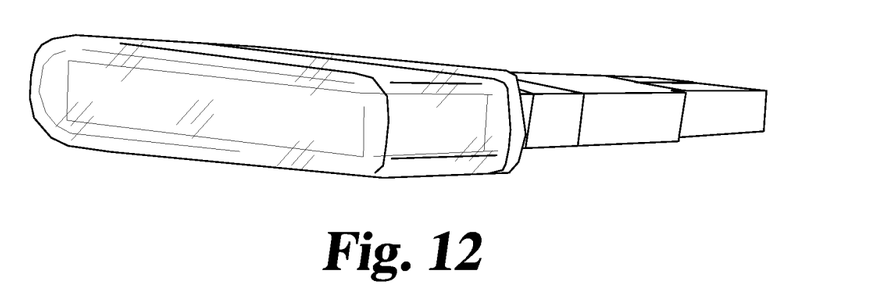
FIG. 12 shows another view of an electrode with a capillary passageway as used in a second embodiment of the test cell of the present invention.
Figure 13:
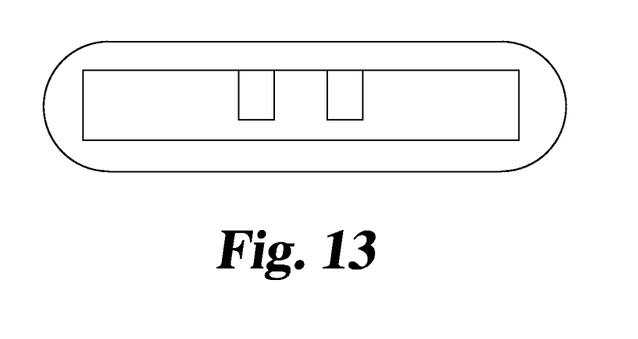
FIG. 13 shows another view of an electrode with a capillary passageway as used in a second embodiment of the test cell of the present invention.

FIG. 9 shows another view of an electrode with a capillary passageway as used in a second embodiment of the test cell of the present invention. Capillary cover 29 is spaced apart from electrode surface 21 a distance effective to cause cleaning fluid to be drawn into and up in the capillary passageway by capillary forces. A gap 30 is provided between capillary cover member 29 and electrode surface 21.

FIGS. 10-13 show additional views of an electrode with a capillary passageway as used in a second embodiment of the test cell of the present invention. The illustrated embodiments include a capillary cover 29 spaced apart from electrode surface 21 a distance effective to cause cleaning that liquid will be drawn into and up in the capillary passageway by capillary forces. The space between capillary cover 29 and electrode surface 21 defines a gap 30.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

Additionally, it is to be appreciated that the elements described herein may be combined in combinations and sub-combinations other than those described as preferred embodiments. Moreover, the inventive devices may comprise any or all combinations of the disclosed elements, or the inventive devices may consist essentially of any or all combinations of the disclosed elements.

The invention claimed is:

1. A test cell for analyzing residue on the surface of a microelectronic component, comprising:
    a) a cleaning tip chamber having:
        i) a first opening for passing fresh cleaning fluids into the chamber and for passing used cleaning fluid out of the chamber,
        ii) a second opening bounded by an end seal and defining a test area in which cleaning fluid may contact the surface of a component to be tested, and
        iii) a third opening for venting the cleaning tip chamber to the atmosphere;
    b) a common cleaning/aspiration passageway communicating with said cleaning tip chamber through said first opening and effective for providing fresh cleaning fluid to said cleaning tip chamber and for removing used cleaning fluid from said cleaning tip chamber,
    c) a cleaning passageway for providing fresh cleaning fluids to said cleaning/aspiration passageway;
    d) an aspiration passageway for removing used cleaning fluid from said cleaning/aspiration passageway; and
    e) an analysis chamber in fluid communication with said aspiration passageway, said analysis chamber having one or more test electrodes disposed therein, wherein said test electrodes are effective for qualitatively and/or quantitatively measuring residue removed from the microelectronic surface by the cleaning fluid.

2. A test cell according to claim 1 wherein said test cell further includes: f) a venting passageway communicating with said cleaning tip chamber through said third opening and effective for venting the cleaning tip chamber to the atmosphere.

3. A test cell according to claim 1 wherein said end seal defines a test area of between about 10 mm$^2$ and about 50 mm$^2$.

4. A test cell according to claim 1 wherein said end seal defines a test area of about 18 mm$^2$.

* * * * *